United States Patent [19]

Sakakura et al.

[11] Patent Number: 4,900,413

[45] Date of Patent: Feb. 13, 1990

[54] PROCESS FOR DIRECT CARBONYLATION OF HYDROCARBONS

[75] Inventors: Toshiyasu Sakakura; Massato Tanaka, both of Yatabemachi, Japan

[73] Assignee: Agency of Industrial Science and Technology, Tokyo, Japan

[21] Appl. No.: 124,649

[22] Filed: Nov. 24, 1987

Related U.S. Application Data

[63] Continuation-in-part of Ser. No. 30,540, Mar. 27, 1987, abandoned.

[30] Foreign Application Priority Data

Sep. 16, 1986 [JP] Japan .................................. 61-217587
Oct. 1, 1986 [JP] Japan .................................. 61-233704

[51] Int. Cl.$^4$ .............................................. B01J 19/08
[52] U.S. Cl. ............................... 204/157.87; 204/157.9; 204/157.93
[58] Field of Search ............... 568/311, 331, 335, 342, 568/425; 204/157.6, 157.65, 157.87, 157.88, 157.9, 157.93

[56] References Cited

U.S. PATENT DOCUMENTS 2,485,237 10/1949 Gresham ............................. 568/428
4,487,972 12/1984 Haag .................................... 568/311

FOREIGN PATENT DOCUMENTS 55-113737 2/1980 Japan ............................. 204/157.84
58-124724 7/1983 Japan ............................... 204/157.9

OTHER PUBLICATIONS

Kunin et al., "Photochemical Carbonylation of Benzene by Iridium(I) and Rhodium(I) Square-Planar Complexes", J. Am. Chem. Soc. 1986, 108, 535-536.
Fisher et al., "Carbon-Hydrogen Bond Activation Using a Bis(phosphine)-Iridium Carbonyl Hydride and the Carbonylation of Benzene", pp. 764-767, Organometallics, vol. 2, No. 6, 1983.

*Primary Examiner*—John F. Niebling
*Assistant Examiner*—Ben C. Hsing
*Attorney, Agent, or Firm*—Armstrong, Nikaido, Marmelstein, Kubovcik & Murray

[57] ABSTRACT

A process is disclosed, for the manufacture of carbonylated products and/or olefins by reacting hydrocarbons with carbon monoxide in the presence of a transition metal complex, under irradiation with light.

10 Claims, No Drawings

PROCESS FOR DIRECT CARBONYLATION OF HYDROCARBONS

This application is a continuation-in-part of application Ser. No. 030,540, filed Mar. 27, 1987, now abandoned.

BACKGROUND OF THE INVENTION

The present invention relates to a process for the direct carbonylation of C—H bonds of hydrocarbons for the production of aldehydes and/or other useful products such as olefins, alcohols, carboxylic acids, ketones, and so forth.

In principle, various useful products such as aldehydes, carboxylic acids, alcohols, ketones and olefins can be produced by directly functionalizing hydrocarbons. In particular, the direct and selective carbonylation of hydrocarbons under mild conditions is of great interest. Although a carbon-to-hydrogen bond of the hydrocarbons must be activated in the carbonylation, the bond energy of the carbon-to-hydrogen bond is high and, therefore the direct carbonylation is thought to be quite difficult. In fact, a process for directly carbonylating hydrocarbons with carbon monoxide in the presence of a metal-complex has substantially been unknown.

An indirect carbonylation process has been employed heretofore which comprises converting a hydrocarbon into an activated compound by oxidation or halogenation, and reacting the compound with carbon monoxide in the presence of a hydrogen source or a nucleophilic reagent. However, the number of the steps of such an indirect carbonylation process is larger than that of the direct carbonylation process, so that the indirect process is not preferred from the viewpoint of saving resources and energy.

On the other hand, complex catalysts are studied recently and investigations are made for the purpose of employing a combination of a complex catalyst with other activation processes for the reaction. In particular, intensive investigations of a combination of the activation by light and a metal-complex are in progress. However, any efficient direct carbonylation processes wherein a hydrocarbon is reacted with carbon monoxide in the presence of a complex catalyst under irradiation with light have not been known yet.

R. Eisenberg et al have made reports on photochemical carbonylation of benzene in the presence of rhodium complex or iridium complex (Organometallics, 1983, 2, 767 and J. Am. Chem. Soc. 1986, 108, 535). According to the reports, the yield attained is extremely low, and since the low yields are due to a thermodynamic limitation, it essentially is difficult to attain an improvement in or relating to the yield. Further, the reports are limited to deal only with reactions of benzene, and in the prior art there is not known an instance of the reaction of olefines.

SUMMARY OF THE INVENTION

An object of the present invention is to provide a process for directly converting hydrocarbons into useful compounds by reacting them with carbon monoxide in the presence of a transition metal complex under irradiation with light. The above object of the present invention is attained by reacting a hydrocarbon having 1 to 50 carbon atoms with carbon monoxide in the presence of a transition metal complex under irradiation with light.

DESCRIPTION OF THE PREFERRED EMBODIMENTS

The present invention relates to a process for directly reacting a hydrocarbon with carbon monoxide by an activation process wherein a combination of a transition metal-complex and irradiation with light is employed.

The hydrocarbons used herein include aliphatic hydrocarbons having 1 to 50 carbon atoms, preferably 1 to 30 carbon atoms, alicyclic hydrocarbons having 3 to 50, preferably 3 to 20 carbon atoms, and aromatic hydrocarbons containing an aromatic ring in the molecule and having 6 to 50 carbon atoms, preferably 6 to 18 carbon atoms. These hydrocarbons may be substituted with a substituent such as an alkoxy, acyl, acyloxy, carboalkoxy or cyano group or a halogen atom. Examples of the aliphatic hydrocarbons unsubstituted or substituted with functional group(s) include methane, ethane, propane, butane, pentane, hexane, heptane, octane, nonane, decane, eicosane and skeletal isomers of them; and ethylene, propylene, butadiene, acetylene, diethyl ether, acetonitrile and 1-fluorohexane. Examples of the alicyclic hydrocarbons include cyclopropane, cyclopentane, cyclohexane and decalin. Examples of the aromatic hydrocarbons include benzene, toluene, o-, m- and p-xylenes, ethylbenzene, hexylbenzene, decylbenzene, styrene, naphthalene, α- and β-methylnaphthalenes, anthracene, diphenyl ether, anisole, benzonitrile, methyl benzoate and benzophenone.

According to the process of the present invention, the above-mentioned hydrocarbons are reacted with carbon monoxide in the presence of a transition metal complex under irradiation with light. Complexes containing a transition metal as the central metal are used as the transition metal complexes. Among them, complexes containing rhodium, iridium, cobalt, ruthenium or iron as the central metal provide particularly preferred results. At least one of the ligands is a monophosphine of the following general formula (I) or a bisphosphine of the following general formula (II):

$$R^1R_2R_3P \qquad (I)$$

wherein $R^1$, $R^2$ and $R^3$ may be the same or different and represent each an alkyl, aralkyl or cycloalkyl group having 1 to 20 carbon atoms, and

$$R^4R^5P-A-PR^6R^7 \qquad (II)$$

wherein $R^4$, $R^5$, $R^6$ and $R^7$ may be the same or different and represent each an alkyl, aralkyl or cycloalkyl group having 1 to 20 carbon atoms and A represents an alkylene, cycloalkylene, arylene, aralkylene or ferrocenylene group having 1 to 20 carbon atoms.

When the phosphine ligand of the catalyst has an excessively high electron-donating capacity, the catalytic activity is low in most reactions conducted in the presence of a complex catalyst. On the contrary, in the carbonylation process of the present invention, the phosphines having a high electron-donating capacity provides good results unlike the usual complex-catalytic reactions. Examples of preferred phosphine ligands include trimethylphosphine, triethylphosphine, tributylphosphine, trioctylphosphine, tricyclohexylphosphine, tribenzylphosphine, 1,2-bis(dimethylphosphino)ethane, 1,4-bis(dimethylphosphino)butane, 1,2- bis(dibutylphosphino)ethane, 1,2-bis(dicyclohexylphosphino)ethane, α,α'bis(dimethylphosphino)-o-xylene and 1,2-bis(dimethylphosphino)cyclohexane. Examples of the transition metal complexes usable herein include RhCl($R^1R^2R^3P$)$_3$, RhCl(CO)($R^1R^2R^3P$)$_2$, RhBr(CO)($R^1R^2R^3P$)$_2$, HRh(CO)($R^1R^2R^3P$)$_3$, HRh(CO)$_2$($R^1R^2R^3P$)$_2$, RhCl(CO)($R^4R^5$P-A-$Pr^6R^7$), IrCl($R^1R^2R^3P$)$_3$, IrCl(CO)($R^1R^2R^3P$)$_2$, IrBr(CO)($R^1R^2R^3P$)$_2$, IrH$_5$($R^1R^2R^3P$)$_2$, IrH$_3$(CO)($R^1R^2R^3P$)$_2$, IrCl(CO)($R^4R^5$P-A-$PR^6R^7$), Cp'RhH$_2$($R^1R^2R^3P$), Cp'IrH$_2$($R^1R^2R^3P$), Co$_2$(CO)$_6$($R^1R^2R^3P$)$_2$, CpCoI$_2$($R^1R^2R^3P$), CoBr$_2$($R^1R^2R^3P$)$_2$, CoCl($R^1R^2R^3P$)$_3$, CoH(N$_2$)($R^1R^2R^3P$)$_3$, CoH$_3$($R^2R^2R^3P$)$_3$, CpCo($R^2R^2R^3P$)$_2$, AcCo(CO)$_3$($R^1$Rhu 2$R^3$P), Fe(CO)$_3$($R^1R^2R^3P$)$_2$ and Ru(CO)$_3$($R^1R^2R^3P$)$_2$, wherein $R^1$ to $R^7$ and A are as defined above, Cp represents a cyclopentadienyl group and Cp' represents a pentamethylcyclopentadienyl group, and Ac represents an acetyl group. The transition metal complexes can be produced prior to the carbonylation by reacting a transition metal compound with carbon monoxide and/or the above-mentioned phosphine or a reagent such as NaBH$_4$, CpNa, Cp'Na or formaldehyde. Alternatively, the complex can be formed in situ and used in the carbonylation directly without isolation thereof. Preferred examples of the transition metal compounds used as the starting material in the formation of the complex in situ are Co$_2$(CO)$_8$, Co$_4$(CO)$_{12}$, Co(NO$_3$)$_2$, CoCl$_2$, CoCO$_3$, Co(acac)$_3$, RhCl$_3$, [RhCl(CO)$_2$]$_2$, [RhCl(1,5-hexadiene)]$_2$, Rh$_4$(CO)$_{12}$, Rh(acac)$_3$, Rh(acac)(CO)$_2$, [RhCl(C$_2$H$_4$)$_2$]$_2$, Na$_2$IrCl$_6$, IrCl$_3$, H$_2$IrCl$_6$, Na$_3$IrCl$_6$, [IrCl)(C$_8$H$_{14}$)$_2$]$_2$, [IrCl(C$_8$H$_{12}$)]$_2$, IrCl(CO)$_3$, Ir$_4$(CO)$_{12}$, Fe(CO)$_5$, Fe$_3$(CO)$_{12}$, Ru(CO)$_5$ and Ru$_3$(CO)$_{12}$.

The wavelength region of the light for the irradiation is ultraviolet and visible ray regions, preferably within a range of 200 to 800 nm. For purposes of the present invention, it may be devised to control the region of wavelengths of light and/or to use light in the form of a monochromatic light. A light of a mercury lamp, a xenon lamp or a sun light is preferably employed. Although the carbonylation process of the present invention can proceed at a temperature of below 0° C., the reaction system can be heated up to 250° C. so as to obtain a preferred reaction rate. The preferred temperature range which varies depending on the structure of the hydrocarbon used in the present invention is usually 0° to 180° C. The pressure of carbon monoxide is preferably in the range of 0.1 to 300 atm, particularly in the range of 0.3 to 100 atm, since the reaction rate is reduced when the pressure is beyond this range.

Although the reaction of the present invention can be conducted usually without using any solvents, a solvent which is more difficultly carbonylated than the hydrocarbon reactant can be used.

The reaction product can be isolated easily by for example, distillation, recrystallization, chromatography or the like.

Thus, according to the process of the present invention, carbonyl compounds such as aldehydes, carboxylic acids, alcohols and ketones as well as other useful compounds such as olefins and dehydrogenative coupling products can be produced by directly reacting easily available hydrocarbons with carbon monoxide and the products can be separated easily. The amount of a formed alcohol can be increased by conducting the carbonylation process of the present invention in the presence of a reducing agent like hydrogen.

When the process of the present invention is compared with a hydroformylation process and cracking process concerning the production of an aldehyde and an olefin, respectively, it is noted that the former is superior to the latters with regard to mildness of the reaction conditions (i.e. ambient temperature and atmospheric pressure) and highness of the regioselectivity.

Therefore, the present invention provides a new efficient process for producing carbonyl compounds and other useful products.

The following examples will further illustrate the present invention.

In the following examples, the products were identified by comparing the retention time in the gas chromatography and the fragmentation pattern in the mass spectrometry thereof with those of standard samples.

EXAMPLE 1:

33 ml of a solution of 66.9 mg (0.21 mmol) of chlorocarbonylbis(trimethylphosphine)rhodium in cyclohexane was placed in a 70-ml Pyrex reactor. After conducting freeze degasification twice, carbon monoxide (1 atm) was introduced therein by means of a rubber baloon. The mixture was stirred at room temperature for 16.5 h under irradiation with an immersion-type 100-W high-pressure mercury lamp. β-Methylnaphthalene was added thereto as the internal reference and the mixture was analyzed according to gas chromatography to quantitatively determine the products. The results were as follows:

| Product | Yield (%/Rh) |
| --- | --- |
| cyclohexanecarboxaldehyde | 10 |
| cyclohexanecarboxylic acid | 3 |

EXAMPLE 2:

The reaction was conducted in the same manner as in Example 1 except that the amount of the rhodium complex was reduced to 1/10 of that used in Example 1 and that 30 ml of cyclohexane was used as the solvent to obtain the following products:

| Product | Yield (%/Rh) |
| --- | --- |
| cyclohexanecarboxaldehyde | 193 |
| cyclohexanemethanol | 245 |
| cyclohexanecarboxylic acid | 149 |

EXAMPLE 3:

The reaction was conducted in the same manner as in Example 2 except that pentane was used as the solvent. It was found that the terminal methyl group was selectively carbonylated as shown below. Butene and acetaldehyde were formed by the light-induced reaction (Norrish type II) of hexylaldehyde.

| Product | Yield (%/Rh) |
| --- | --- |
| caproaldehyde | 2725 |
| 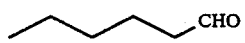 | |
| 2-methylvaleraldehyde | <30 |

-continued

| Product | Yield (%/Rh) |
|---|---|
| 2-ethylbutyraldehyde (CHO structure) | not detected |
| (CHO structure) | |

EXAMPLE 4:

The reaction was conducted in the same manner as in Example 2 except that decane was used as the solvent to obtain the following products:

| Product | Yield (%/Rh) |
|---|---|
| n-undecyl aldehyde | 1462 |
| 2-methyldecanal | <42 |
| n-undecanol | 284 |
| 1-nonene | 2861 |
| trans-2-nonene | 17 |
| cis-2-nonene | 6 |
| acetaldehyde | 798 |
| ethanol | 671 |

EXAMPLE 5:

The reaction was conducted in the same manner as in Example 2 under an atmosphere of a gaseous mixture of methane and carbon monoxide in a ratio of 1:1 in order to carbonylate methane. Acetaldehyde and ethanol were detected.

EXAMPLE 6:

The reaction was conducted in the same manner as in Example 2 under an atmosphere of a gaseous mixture of ethylene and carbon monoxide in a rtio of 1:1 to recognize that acrolein was produced.

EXAMPLE 7:

30 ml of a solution of 66.9 mg (0.21 mmol) of chlorocarbonylbis(trimethylphosphine)rhodium in benzene was placed in a 70-ml Pyrex reactor. After conducting freeze degasification twice, carbon monoxide (1 atom) was introduced therein by means of a rubber baloon. The mixture was stirred at room temperature for 16.5 h under irradiation with an immersion-type 100-W high-pressure mercury lamp. β-Methylnaphthalene was added thereto as the internal reference and the mixture was analyzed according to gas chromatography to quantitatively determine the products. The results were as follows:

| Product | Yield (%/Rh) |
|---|---|
| benzaldehyde | 1544 |
| benzyl alcohol | 147 |
| benzoic acid | 5 |
| biphenyl | 35 |
| benzophenone | 54 |

EXAMPLES 8 TO 13 AND COMPARATIVE EXAMPLES 1 to 11:

The reaction was conducted in the same manner as in Example 7 in the presence of each of the catalysts shown in Table 1 below. The results of Examples 7 to 13 and Comparative Examples 1 to 11 are also shown in Table 1.

TABLE 1

| Example or Comparative Example | Catalyst | Yield (%/Rh) PhCHO | PhCH$_2$OH |
|---|---|---|---|
| Example 7 | RhCl(CO)(PMe$_3$)$_2$ | 1544 | 147 |
| Comp. Ex. 1 | RhCl(CO)(PPh$_3$)$_2$ | 29 | 0 |
| Comp. Ex. 2 | RhCl(CO)[P(OMe)$_3$] | 16 | 0 |
| Example 8 | RhCl(CO)(PEt$_3$)$_2$ | 328 | 4 |
| Example 9 | RhCl(CO)(Me$_2$PCH$_2$CH$_2$PMe$_2$) | 130 | 2 |
| Comp. Ex. 3 | Rh$_4$(CO)$_{12}$ | trace | 0 |
| Comp. Ex. 4 | [RhCl(CO)$_2$]$_2$ | trace | 0 |
| Comp. Ex. 5 | RhH(CO)(PPh$_3$)$_3$ | 0$^{(a)}$ | 0$^{(a)}$ |
| Comp. Ex. 6 | IrCl(CO)(PPh$_3$)$_2$ | 0 | 0 |
| Comp. Ex. 7 | RhCl(CO)(Ph$_2$PCH$_2$CH$_2$PPh$_2$) | 2 | 0 |
| Comp. Ex. 8 | RhCl(CO)$_2${P(C$_6$H$_4$-CH$_3$)$_3$} | 0 | 0 |
| Comp. Ex. 9 | IrBr(CO)(PPh$_3$)$_2$ | 0 | 0 |
| Comp. Ex. 10 | RhBr(CO){P(C$_6$H$_4$-CH$_3$)$_3$}$_2$ | 9 | 0 |
| Comp. Ex. 11 | (C$_5$Me$_5$)Rh(CO)$_2$ | 0 | 0 |
| Example 10$^{(b,c)}$ | RhCl(CO)(PMe$_3$)$_2$ | 6517 | 738 |
| Example 11$^{(b)}$ | Rh(SCN)(CO)(PMe$_3$)$_2$ | 5667 | 742 |
| Example 12$^{(b)}$ | RhCl(CO)(PBu$_3$)$_2$ | 1853 | 197 |

TABLE 1-continued

| Example or Comparative Example | Catalyst | Yield (%/Rh) PhCHO | PhCH₂OH |
|---|---|---|---|
| Example 13[b] | RhCl(CO){P(CH₂O)₃CMe}₂ | 3329 | 732 |

Notes:
[a]The yield of tolualdehyde and that of methylbenzyl alcohol when the reaction was operated in toluene.
[b]The concentration of the complex was set at 0.7 mM.
[c]Yields of the products (%/Rh):
PhCO₂H: 108
Ph—Ph: 215
PhCOPh: 688

EXAMPLES 14 TO 21:

The reaction was conducted in the same manner as in Example 7 except that various hydrocarbons were used as the reactant. The results are shown in Table 2.

TABLE 2

| Example | X:X—⌬ | Rh concn. (mM) | X—⌬—CHO (%/Rh) (o:m:p) | X—⌬—CH₂OH (%/Rh) (o:m:p) | Other product (%/Rh) |
|---|---|---|---|---|---|
| 14 | CH₃— | 7 | 1525 2:63:35 | 200 8:72:21 | PhCH₂CHO 13 PhCH₂CH₂Ph 30 CH₃C₆H₄CO₂H 6 CH₃C₆H₄COC₆H₄CH₃ 68 |
| 15 | CH₃— | 0.7 | 3909 0.5:53.5:46 | 3354 3:71:26 | PhCH₂CH₂Ph 2165 CH₃C₆H₄COC₆H₄CH₃ 650 CH₃C₆H₄CO₂H 59 |
| 16 | CH₃O— | 7 | 566 12:54:34 | 93 26:69:5 | |
| 17 | CH₃O— | 0.7 | 3930 7:52:41 | 993 37:59:4 | |
| 18 | Cl— | 7 | 115 41:36:23 | 37 70:20:10 | Ph—C₆H₄Cl 14 |
| 19 | Cl— | 0.7 | 33 | 4 | Ph—C₆H₄Cl 695 |
| 20 | NC— | 7 | 82 1:85:14 | 0 | |
| 21 | NC— | 0.7 | 65 4:82:14 | 62 m:p = 77:23 | |

EXAMPLE 22:

The reaction was conducted in the same manner as in Example 10 except that chlorocarbonylbis(trimethylphosphine)iridium was used as the catalyst to produce benzaldehyde (42%/Ir).

EXAMPLE 23:

The reaction was conducted in the same manner as in Example 10 except that cyclohexane saturated with naphthalene was used as the solvent to produce a mixture of α- and β-naphthaldehydes (54 and 78%/Rh, respectively). A mixture of α- and β-naphthalene methanol was also detected (115 and 128%/Rh, respectively).

EXAMPLE 24:

The reaction was conducted in the same manner as in Example 15 except that chlorotris(tributylphosphine)cobalt was used as the catalyst to produce a mixture of o-, m- and p-tolualdehydes.

EXAMPLE 25:

The reaction was conducted in the same manner as in Example 7 in an atmosphere of a synthesis gas comprising hydrogen and carbon monoxide in a ratio of 1:1 to produce 876%/Rh of benzaldehyde and 314%/Rh of benzyl alcohol. The ratio of the alcohol/aldehyde was far higher than that obtained in Example 7.

EXAMPLE 26:

20 ml of a solution of 0.14 mmol of chlorocarbonylbis(trimethylphosphine)rhodium in benzene was placed in a 40-ml Hastelloy autoclave provided with a Pyrex aperture plate under a nitrogen atmosphere. Carbon monoxide (40 atm) was introduced therein and the reaction was conducted at room temperature for 16.5 h under irradiation with a light of a 500-W high-pressure mercury lamp of external irradiation type. The reaction solution was analyzed according to gas chromatography. 16%/Rh of benzaldehyde was detected.

EXAMPLE 27:

The reaction was conducted in the same manner as in Example 26 except that the pressure of carbon monoxide and reaction temperature were 5 atm and 100° C. respectively. 7%/Rh of benzaldehyde was produced.

EXAMPLE 28:

The reaction was conducted in the same manner as in Example 7 except that pentahydridobis(triisopropylphosphine)iridium was used as the catalyst to produce 7%/Rh of benzoic acid and a trace amount of benzaldehyde.

EXAMPLE 29:

Except that heptadecane was used for the solvent, a same reaction as in Example 2 was operated to ascertain the formation of 1187%/Rh of octadecanal and 219%/Rh of hexadecene.

EXAMPLE 30:

Except that for the complex, tricarbonylbis(trimethylphosphine)iron was used in place of the rhodium complex, a same reaction as in Example 10 was operated, and as a result of this, there was formed 0.3%/Fe of benzaldehyde.

EXAMPLE 31:

Except that for the complex, tricarbonylbis(triethylphosphine)ruthenium was used in place of the rhodium complex, a same reaction as in Example 10 was operated, and as a result of this, there were formed 28%/Ru of benzaldehyde and 13%/Ru of benzyl alcohol.

EXAMPLE 32:

Except that for the complex, acetyltricarbonyltriethylphosphine cobalt was used in place of the rhodium complex, a same reaction as in Example 10 was operated, and as a result of this, there were formed 1%/Co of benzaldehyde and 6%/Co of benzyl alcohol.

EXAMPLE 33:

A solution (2 ml) in benzene of chlorocarbonylbis(trimethylphosphine)rhodium (0.7 mM) was charged in a Pyrex-made 1-cm rectangular cell, and carbon monoxide was introduced into the cell after the pressure inside the cell was reduced. Then, the solution was subjected to irradiation of sunlight rays condensed through lenses, for about 7 hours, to obtain the following products.

| Benzaldehyde | 112 %/Rh |
| Benzyl alcohol | 5 %/Rh |

EXAMPLE 34:

Using chlorodicarbonylrhodium dimer and trimethylphosphine (phosphorus/rhodium=2/1) in place of chlorocarbonylbis(trimethylphosphine)rhodium, a same reaction as in Example 2 was operated to obtain the following products:

| Cyclohexanecarbaldehyde | 158 %/Rh |
| Cyclohexane methanol | 112 %/Rh |
| Cyclohexane carboxylic acid | 55 %/Rh |

EXAMPLES 35 TO 38:

With the irradiation wavelength varied as shown in Table 3 below, carbonylation reactions of decane were operated to obtain results as shown also in Table 3. Reactions were carried out in a 1-atm carbon monoxide atmosphere in a Pyrex-made 1-cm rectangular cell, using chlorocarbonylbis(trimethylphosphine)rhodium. Irradiation of light was made, using a 500-W high-pressure mercury lamp, with the wavelengths controlled, using a glass filter.

TABLE 3

| Example | Irradiation wavelength[a] (nm) | Time (h) | $C_{9-n}-C-C_n$ $\mid$ CHO (n = 0:1:2:3:4) | nonene 1- | 2-trans | 2-cis |
|---|---|---|---|---|---|---|
| 35 | 295–420 | 5.0 | 610 (86:5:4:2:3) | 319 | 0 | 0 |
| 36 | >325 | 5.0 | 126 (8:45:17:15:16) | 0 | 0 | 0 |
| 37 | >325 | 16.5 | 559 (6:44:17:16:17) | 0 | 0 | 0 |
| 38 | >375 | 16.5 | 32 (0:49:18:17:17) | 0 | 0 | 0 |

RhCl(CO)(PMe$_3$)$_2$ 0.7 mM, CO 1 atm. room temperature, irradiated with a 500 W high pressure mercury lamp
[a]Ranges where the transmittance is over 10%.

EXAMPLES 39 TO 41:

With the irradiation wavelength varied as shown in Table 4 below, carbonylation reactions of benzene were conducted in same manners as in Example 35, to obtain results as shown also in Table 4.

TABLE 4

| Example | Wavelength[a] (nm) | Time (h) | Yield (%/Rh) PhCHO | PhCH$_2$OH |
|---|---|---|---|---|
| 39 | 295–420 | 6 | 283 | 6 |
| 40 | >325 | 6 | 54 | 0 |
| 41 | >375 | 18 | tr | 0 |

RhCl(CO)(PMe$_3$)$_2$ 0.7 mM, CO 1 atm, room temp.

EXAMPLES 42 AND 43:

With the phosphine ligand of the complex varied as shown in Table 5 below, the carbonylation reaction in Example 35 under the condition of the irradiation wavelength >325 nm was repeated to obtain results as shown also in Table 5.

TABLE 5

| Example | Ligand | Cone angle | $C_{9-n}-C-C_n$ $\mid$ CHO Yield (%/Rh)[a] (n = 0:1:2:3:4) |
|---|---|---|---|
| 42 | PBu$_3$ | 130° | 281 (8:59:13:10:11) |
| 43 | P(i-Pr)$_3$ | 160° | 194 (45:39:7:5:4) |

RhCl(CO)(PR$_3$)$_2$ 0.7 mM, CO 1 atm, room temp., 16.5 h, Irradiation wavelength: >325 nm.
[a]Olefins were not formed.

We claim:
1. A process for the direct carbonylation of a hydrocarbon which comprises reacting a hydrocarbon, selected from the group consisting of an aliphatic, an alicyclic, and an aromatic hydrocarbon, with carbon monoxide under irradiation with light in the presence of a complex of a metal of Group VIII of the periodic table, wherein a ligand in said complex is a phosphine selected from the group consisting of a monophosphine of the formula $R^1R^2R^3P$ and a bisphosphine of the formula $R^4R^5P$-A-$PR^6R^7$, wherein $R^1$, $R^2$, $R^3$, $R^4$, $R^5$, $R^6$ and $R^7$, which are the same or different, are each a member selected from the group consisting of alkyl, aralkyl, and cycloalkyl; and A is a member selected from the group consisting alkylene, cycloalkylene, arylene, aralkylene and ferrocenylene.

2. The process according to claim 1, wherein the metal is a member selected from the group consisting of rhodium, iridium, cobalt, ruthenium and iron.

3. The process according to claim 1, wherein $R^1$, $R^2$, $R^3$, $R^4$, $R^5$, $R^6$ and $R^7$ are each an alkyl group, an aralkyl group or a cycloalkyl group having 1 to 20 carbon atoms, and A is an alkylene group, a cycloalkylene group, an arylene group, an aralkylene group or a ferrocenylene group having 1 to 20 carbon atoms.

4. A process according to claim 1, wherein the hydrocarbon is an aliphatic or alicyclic hydrocarbon having 1 to 30 and 3 to 20 carbon atoms, respectively.

5. A process according to claim 1, wherein the hydrocarbon is an aromatic hydrocarbon having 6 to 18 carbon atoms.

6. A process according to claim 1, wherein the light for the irradiation ranges from ultraviolet to visible ray regions.

7. A process according to claim 1, wherein the reaction is conducted at a temperature of 0° to 180° C.

8. A process according to claim 1, wherein the reaction is conducted at a pressure in the range of 0.3 to 100 atm.

9. A process according to claim 1, wherein the reaction is conducted in the presence of hydrogen.

10. A process according to claim 1, wherein the reaction is conducted in the absence of hydrogen.

* * * * *

UNITED STATES PATENT AND TRADEMARK OFFICE
CERTIFICATE OF CORRECTION

PATENT NO. : 4,900,413
DATED : February 13, 1990
INVENTOR(S) : SAKAKURA et al

It is certified that error appears in the above-identified patent and that said Letters Patent is hereby corrected as shown below:

On the cover page, Item [75], "Massato Tanaka" should read --Masato Tanaka--.

Column 1, line 59, "olefines" should read --paraffins--.

Column 3, line 15, "AcCo(CO)$_3$(R$^1$Rhu2R$^3$P)" should read --AcCo(CO)$_3$(R$^1$R$^2$R$^3$P)--;

line 29, "Cocl$_2$" should read --CoCl$_2$--.

Column 4, line 59, "hexylaldehyde" should read --hexanal--.

Column 5, line 21, "n-undecyl aldehyde" should read --undecanal--.

Column 6, line 5, "rtio" should read --ratio--.

Signed and Sealed this

Twenty-fifth Day of June, 1991

Attest:

HARRY F. MANBECK. JR.

Attesting Officer

Commissioner of Patents and Trademarks